United States Patent
Ozero

[11] 3,964,980
[45] June 22, 1976

[54] PROCESS FOR THE RECOVERY OF ETHYLENE OXIDE

[75] Inventor: Brian I. Ozero, New York, N.Y.

[73] Assignee: Halcon International, Inc., New York, N.Y.

[22] Filed: Mar. 24, 1975

[21] Appl. No.: 561,515

[52] U.S. Cl. .................................. 203/42; 203/69; 203/96; 55/51; 260/348.5 R
[51] Int. Cl.² .......................................... C01D 1/14
[58] Field of Search ............... 203/42, 69, 98, 4, 96; 260/348.5 R; 55/46, 48, 51

[56] References Cited
UNITED STATES PATENTS

| | | | |
|---|---|---|---|
| 3,165,539 | 1/1965 | Lutz .......................................... | 55/51 |
| 3,174,262 | 3/1965 | Lutz .......................................... | 55/51 |
| 3,418,338 | 12/1968 | Gilman et al. ........................ | 203/42 |
| 3,523,957 | 8/1970 | Tsao ............................. | 260/348.5 R |
| 3,729,899 | 5/1973 | Cunningham .......................... | 55/51 |
| 3,745,092 | 7/1973 | Vanderwater ................ | 260/348.5 R |
| 3,766,714 | 10/1973 | Cunningham .......................... | 55/51 |

Primary Examiner—Wilbur L. Bascomb, Jr.
Attorney, Agent, or Firm—William C. Long; David Dick; Riggs T. Stewart

[57] ABSTRACT

The conventional process for the recovery of ethylene oxide produced by the silver catalyzed, vapor phase, partial oxidation of ethylene with molecular oxygen involves a sequence of steps including absorption in water of the ethylene oxide contained in the reaction effluent. The ethylene oxide-containing absorbate is then stripped and the vapor thus generated is subjected to reabsorption, also in water. This invention provides an improved stripper-reabsorption system and includes the steps of partial condensation of the stripper overhead and introduction of an additional absorbent stream into the readsorption step.

6 Claims, 3 Drawing Figures

PROCESS FOR THE RECOVERY OF ETHYLENE OXIDE

THE FIELD OF THE INVENTION

This invention relates to the recovery of ethylene oxide from the gaseous effluent obtained by the silver catalyzed, vapor phase, partial oxidation of ethylene with molecular oxygen. More specifically, this invention relates to an improved stripper-reabsorber system for use in such a recovery operation.

BACKGROUND OF THE INVENTION

When ethylene oxide is prepared by the silver catalyzed, vapor phase, partial oxidation of ethylene with molecular oxygen, a gaseous reaction effluent is obtained. This effluent is extremely dilute with respect to the desired ethylene oxide product, normally containing only from about 0.3 mole % to about 5 mole % of this desired material. Recovery of the ethylene oxide from this effluent gas, as conventionally practiced, involves an initial water absorption step, followed by a stripping step, which is in turn followed by a reabsorption step. See, for example, U.S. Pat. No. 3,418,338.

In such a sequence, the function of the absorption step is to selectively absorb the ethylene oxide from the gaseous reaction effluent with but minimal concurrent absorption of other materials such as unconverted reactants, reaction diluents and reaction by-products which are also present in the reaction effluent. However, as the absorber operates at relatively high pressure, only slightly below that of the reactor, substantial amounts of such materials present in the reaction effluent as carbon dioxide, and any trace impurities such as aldehydic and acidic by-products formed during the oxidation reaction, are concurrently absorbed with the ethylene oxide. In the stripper the absorbed ethylene oxide is re-volatilized by steam stripping as also are substantial amounts of the carbon dioxide and the aldehydic trace impurities originally co-absorbed with the ethylene oxide. The function of the reabsorber is to separate between the ethylene oxide and the carbon dioxide volatilized within the stripper. Thus, within the reabsorber, the stripper overhead is countercurrently contacted with water to obtain, as a bottoms product, a liquid reabsorbate consisting essentially of ethylene oxide and water but also containing residual quantities of carbon dioxide, aldehydic and acidic trace impurities.

As indicated, the absorber operates at relatively high pressure, while both the stripper and reabsorber operate at pressures which are relatively close to atmospheric. This pressure differential facilitates the separations desired in the stripper-reabsorption system, primarily the separation between ethylene oxide and carbon dioxide.

However, this system is possessed of some disadvantages accentuated by the need for obtaining over higher purity products at minimum cost. Temperatures within the stripper are high enough to thermally hydrate a portion of the ethylene oxide to ethylene glycol which, being contaminated by trace impurities, is difficult to upgrade for uses requiring extremely high purity products such as fibers, or even to those requiring lesser purities, such as anti-freeze. Attempts to lower stripper pressure and thus attain lower temperatures within the stripper are generally unattractive since this also lowers pressure within the reabsorber unless vapor compression facilities are provided between the stripper and the reabsorber. Compression facilities have been found to be expensive, difficult to maintain and potentially hazardous. Without compression, however, the lower the pressure within the stripper, the lower will be the pressure within the reabsorber and the greater will be the quantity of water required to preferentially absorb the ethylene oxide within the reabsorber. This, in turn, means that the reabsorber bottoms product (hereinafter referred to as the "reabsorbate"— a solution of ethylene oxide in water) becomes more dilute with respect to ethylene oxide; consequently, subsequent processing to recover ethylene oxide therefrom becomes more expensive and difficult.

Even when the reabsorbate is not to be processed for the recovery of ethylene oxide but rather is to be subjected to thermal hydration for conversion of the ethylene oxide dissolved therein directly to monoethylene glycol (with concomitant formation of higher glycols), the prior art systems present certain problems. The trace impurities dissolved in the reabsorbate interfere with glycol quality. Secondly, the economics of glycol production from the reabsorbate strongly favor the use of solutions relatively concentrated with respect to dissolved ethylene oxide since reabsorbate solutions containing less than, say, 5% by weight of ethylene oxide are difficult to economically employ in glycol production.

These problems have been further accentuated by recent developments in the oxidation reaction. These recent developments entail the use of large concentrations of carbon dioxide as a reaction diluent in the oxidation step (see Belgian patent No. 781,107). Correspondingly, a greater proportion of carbon dioxide is absorbed in the absorber, stripped in the stripper and thus is present in the feed gas to the reabsorber. In turn, this necessitates a substantially increased water rate to the reabsorber and results in a reabsorbate solution more dilute with respect to ethylene oxide.

The art is therefore faced with a need for a stripper-reabsorber system for use in an ethylene oxide recovery process which is readily operated, causes minimal glycol formation and which gives minimum carryover of trace impurities. Additionally, to take advantage of recent developments in the conduct of the oxidation reaction, such a system should be capable of processing materials having high carbon dioxide contents without concomitantly giving an aqueous reabsorbate solution excessively dilute with respect to ethylene oxide. Such a system is provided by this invention.

SUMMARY OF THE INVENTION

In accordance with this invention a basically conventional stripper-reabsorber system is employed with two major modifications. The first of these requires that the stripper overhead vapor be subjected to a partial condensation so that at least about 50% of the water but not over about 20% of the ethylene oxide contained therein are condensed. The condensate is returned as reflux to the stripper. The uncondensed stripper vapor, as in the conventional recovery system, is fed forward and introduced to a lower portion of the reabsorber while water is concurrently introduced to an upper portion of the reabsorber. Thus, within the reabsorber the stripper overhead vapor and water are countercurrently contacted to effect the preferential reabsorption of ethylene oxide to produce the desired reabsorbate solution.

The second modification requires the division of the reabsorbate into two portions, the first of which is cooled and recycled for introduction to the reabsorber at a point intermediate between the points at which the stripper overhead vapor and the water are introduced to the reabsorber. The second portion of the reabsorbate is fed forward to further processing for (a) recovery of ethylene oxide therefrom or (b) for conversion of the ethylene oxide dissolved therein to ethylene glycols or (c) split into two portions, one for ethylene oxide recovery and the other for conversion to ethylene glycols. The relative proportions of the two portions of the reabsorbate are such that the first (which is recycled) is at least 0.2 part by weight per part by weight of net reabsorbate fed forward for further processing.

DESCRIPTION OF THE INVENTION

A further understanding of this invention will be facilitated by reference to the annexed drawing, made up of three figures in which.

Figure 1:
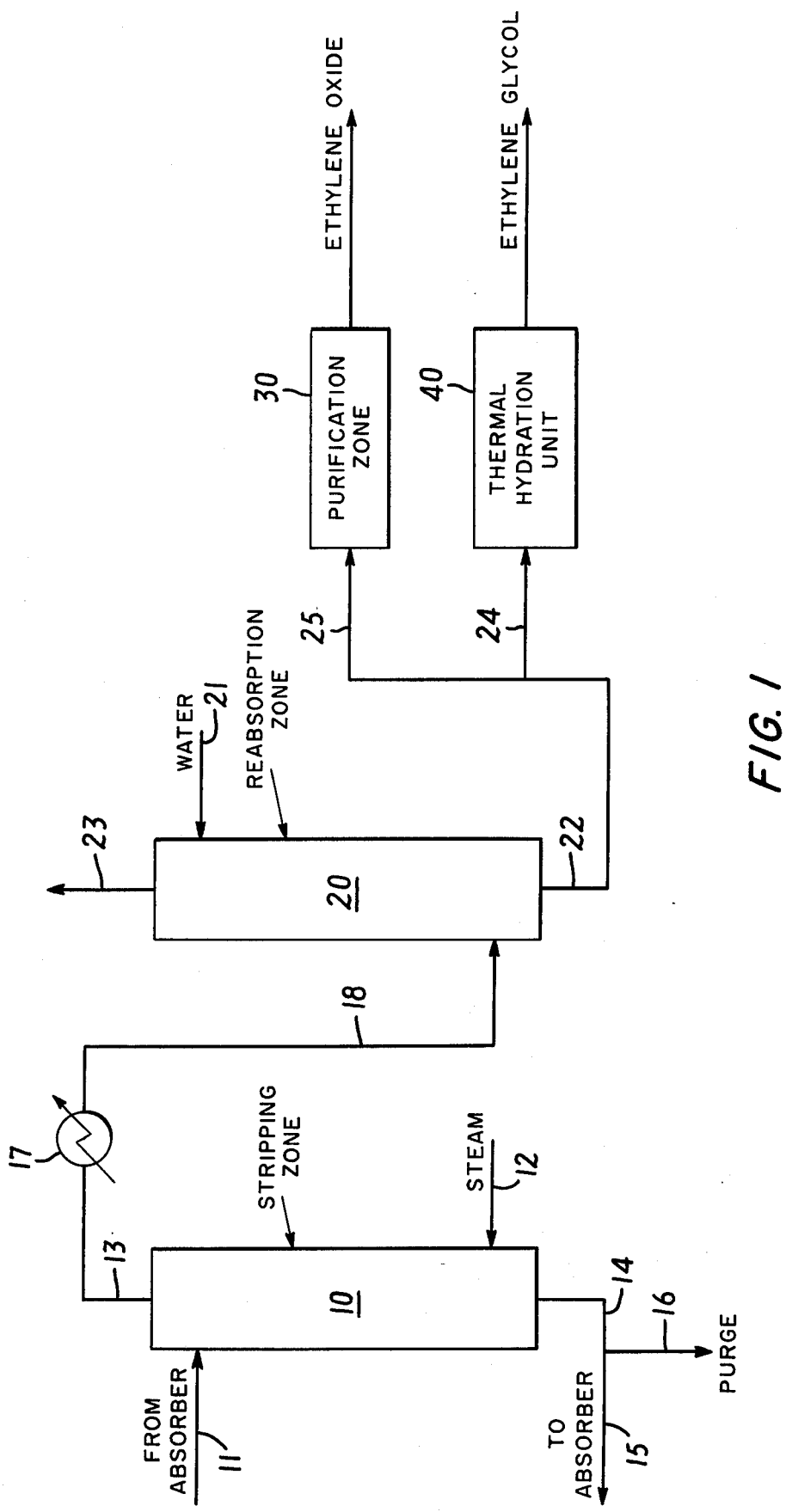
FIG. 1 is a schematic representation of the prior art stripper-reabsorber system and is not illustrative of this invention.

Referring first to FIG. 1, aqueous scrubber liquid (absorbate) obtained by the water scrubbing of a gaseous reaction effluent produced by the silver catalyzed, vapor phase, partial oxidation of ethylene with molecular oxygen is introduced to an upper portion of stripper 10 via conduit 11. Steam is introduced to a lower portion of stripper 10 via conduit 12. By counter-current contact of the absorbate and the steam within stripper 10 the absorbate is stripped of the ethylene oxide dissolved therein, and the ethylene oxide, in admixture with steam and also containing substantial proportions of carbon dioxide as well as trace impurities, is withdrawn from the top of stripper 10 via conduit 13. The stripped absorbate, no longer containing a significant quantity of dissolved ethylene oxide, is withdrawn from the bottom of stripper 10 via conduit 14 and can, after cooling, be returned via conduit 15 to the absorber for re-use in the recovery of ethylene oxide. To prevent uncontrolled buildup of glycols formed in the stripper and of trace impurities, a portion of the stripped absorbate can be purged from the system via conduit 16 for further processing or for discard.

In a typical operation, feed to the stripper may contain from about 0.5 to about 5 wt. % of ethylene oxide, and the stripper is so operated as to recover well over 90%, commonly over 95% and usually over 99% of the ethylene oxide contained in the stripper feed (i.e., the absorbate).

To facilitate the stripping operation conducted within stripper 10, the stripper normally contains a plurality of vapor-liquid contacting devices (trays, plates, packing, etc.) equivalent to at least about 3 theoretical vapor-liquid contacting stages and preferably at least about 5 such stages. More stages can, of course, be employed, though economic considerations would normally preclude use of strippers containing more than about 50 theoretical vapor-liquid contacting stages. Generally strippers having from about 5 to about 40 theoretical vapor-liquid contacting stages, desirably from about 6 to about 30 and preferably from about 7 to about 20 vapor-liquid contacting stages are used.

The efficiency with which the stripping operation is carried out is, of course, a function of the amount of stripping steam provided via conduit 12 in relation to the amount of absorbate entering stripping zone 10 via conduit 11, as well as the number of stripping stages employed. On a molar basis, the ratio of the quantity of steam supplied to the quantity of absorbate introduced should generally be at least 0.03, desirably at least 0.04, and preferably at least 0.05. Greater ratios of steam to absorbate can be employed though there is little advantage to be gained by using ratios in excess of about 0.2 mole of steam per mole of absorbate fed. Normal practice would call for use of ratios from about 0.03 to about 0.20, desirably from about 0.04 to about 0.10 and preferably from about 0.04 to about 0.08 mole of steam per mole of absorbate fed. These ratios of steam to absorbate, of course, presuppose certain stripper pressures, normally from about 1.04 kg/cm$^2$ abs. to about 3.8 kg/cm$^2$ abs., desirably from about 1.1 to about 3.0 and preferably from about 1.2 to about 2.5 kg/cm$^2$ abs. To some extent, the foregoing ratios of steam to absorbate also depend upon the number of theoretical vapor-liquid contacting stages within the stripping zone, i.e., more stages could result in a lessened need for steam, although the foregoing ratios would be appropriate for strippers containing from about 3 to about 20 (or even more) theoretical vapor-liquid contacting stages. Use of more such stages to reduce steam requirements would seldom be economic because of increased stripping zone pressure drop and consequent higher stripping zone bottoms temperatures which would, in turn, cause increased thermal hydrolysis of ethylene oxide to ethylene glycols.

With this conventional from of stripper, the overhead vapor withdrawn via conduit 13 generally contains from about 10 to about 40 mole % ethylene oxide, commonly from about 15 to about 30 mole % of ethylene oxide and usually from about 18 to about 25 mole % of ethylene oxide. The primary diluent in this vapor stream is water, although up to about 15 mole %, commonly up to about 10 mole % but usually not more than about 7–8 mole % of this stream can be generally referred to as non-condensable gases, predominantly $CO_2$ but also perhaps including nitrogen, argon, oxygen, ethane, ethylene, and the like.

With further reference to FIG. 1, it is to be noted that open steam is depicted as injected into the column. This, however, while preferred, is unnecessary since, as the stripper bottoms withdrawn via conduit 14 consists essentially of water, steam can as readily be generated in situ by provision of appropriate reboiling facilities, heating coils, etc.

The overhead vapors withdrawn from stripper 10 via conduit 13 are then cooled in heat exchanger 17 to the maximum economic extent, usually to a temperature within the range of from about 25° C. to about 80° C. and preferably from about 30° C. to about 60° C. and are thereby partially condensed. The mixture of liquid and vapor thus formed is then introduced into a lower portion of reabsorber 20 via conduit 18. Water is introduced to an upper portion of reabsorber 20 via conduit 21. Within reabsorber 20, the stripper overhead vapor and the water are countercurrently contacted to absorb as much as possible to the ethylene oxide entering the reabsorber via conduit 18. Generally 90 mole % of the ethylene oxide, commonly over 95 mole % of the ethylene oxide and usually over 99 mole % of the ethylene oxide is reabsorbed in this manner. The ethylene oxide-water solution thus formed is withdrawn from the bottom of the reabsorber via conduit 22, while the unabsorbed vapors containing the preponderant amount of the $CO_2$ entering the system via conduit 11 together with other non-condensable gases (e.g., ethylene, oxygen, nitrogen, argon, etc.) are vented from the top of the reabsorber via conduit 23 and can be discarded or further treated, for example, for the recovery of the trace amounts of ethylene present or for the recovery of a purified $CO_2$ product, as desired. The reabsorbate solution withdrawn from reabsorber 20 via conduit 22 thus consists essentially of ethylene oxide and water, containing only trace amounts of dissolved $CO_2$ and trace impurities, and can be introduced into purification zone 30 via conduit 25. Alternatively, all or a portion of the reabsorbate can be directly introduced to thermal hydration unit 40 via conduit 40 via conduit 24, in which case the ethylene oxide dissolved in the reabsorbate is converted to ethylene glycols under the influence of heat and pressure.

As in the case of stripper 10, reabsorber 20 also contains a plurality of vapor-liquid contacting devices to promote the countercurrent contact of the water introduced to reabsorber 20 via conduit 21 and the stripper overhead vapor introduced to reabsorber 20 via conduit 18. A number of such devices sufficient to provide at least about 5, desirably at least about 7 and preferably at least about 10 theoretical vapor-liquid contacting stages are provided within reabsorber 20. There is, of course, no upper limit in the number of such stages that can be provided except an economic one. Such economic considerations would normally dictate employment of less than about 50, desirably less than about 40 and preferably less than about 30 theoretical vapor-liquid contacting stages within the reabsorber. Also, as those skilled in the art will recognize, the amount of water necessary to effect the desired reabsorption within the reabsorber is a function of the reabsorber pressure and the number of moles of vapor rising up through the reabsorber. Denominating the number of moles of uprising vapor (referred to as "V" for convenience) as the arithmetic average of the moles of vapor entering the reabsorber via conduit 18 and the number of moles of vapor leaving the reabsorber via conduit 23, the moles of water introduced via conduit 21 (referred to as "L" for convenience) should generally be such as to provide an L/V ratio which generally should be from about 5 to about 50, desirably from about 8 to about 40 and preferably from about 10 to about 30. The foregoing L/V ratios presuppose a reabsorber operating at an overhead pressure from about 1.0 kg/cm$^2$ abs. to about 3.8 kg/cm$^2$ abs., desirably from about 1.05 to about 3.0 and preferably from about 1.1 to about 2.0 kg/cm$^2$ abs., the readsorber overhead pressure being at least marginally lower than that of the stripper.

In this fashion, the prior art reabsorbate solutions obtained contain 5–25 wt. % ethylene oxide, with the balance consisting essentially of water with small amounts, generally less than 1 wt. %, of impurities, predominantly dissolved carbon dioxide and ethylene glycol. More commonly, the reabsorbate contains from about 7 to about 20 wt. % ethylene oxide and preferably it contains from about 8 wt. % to about 15 wt. % ethylene oxide. The system of the present invention provides reabsorbate solutions of comparable composition but these compositions can be achieved by this process with absorbate streams of more widely varying composition than those conventionally encountered.

Further study of the prior art stripper reabsorber system depicted in FIG. 1 indicates certain characteristics of operation which are important. It is apparent that the vapor leaving stripper 10 must be at a sufficiently high pressure to be foreced by means of a pressure gradient, not only through heat exchanger 17 but also through the totality of reabsorber 20 and still retain sufficient pressure to be capable of being vented via conduit 23. In other words, the lowest pressure in a system such as that depicted in FIG. 1 must be at conduit 23, and this pressure must be at least marginally above atmospheric if compression facilities are to be avoided. In order to provide this pressure gradient, the pressure within stripper 10 must be significantly above atmospheric even though most economic stripper operation (with but minimal ethylene oxide hydration) would otherwise call for lowest possible stripper pressure because with higher stripper pressure, the temperature in the stripper will be higher. In balance, therefore, the pressure differential between stripper and reabsorber would generally be no more than 0.5 kg/cm$^2$, commonly be no more than 0.3 kg/cm$^2$, and usually be no more than 0.2 kg/cm$^2$. To minimize the size of interconnecting piping and to allow for necessary instrumentation and control devices, howver, a pressure differential must exist between the stripper overhead and the reabsorber bottoms which would generally be at least 0.01 kg/cm$^2$. Further, any increase in the rate of water introduction via conduit 21 (i.e., an increasing L/V ratio within reabsorber 20) would have a tendency to increase the pressure drop within reabsorber 20 and to mandate yet higher stripper temperatures and, even more disadvantageously, would result in a more dilute reabsorbate solution withdrawn via conduit 22.

When, for example, the process of Belgian patent No. 781,107 is employed in the oxidation step, the quantity of non-condensable gases in stripper overhead 13, and consequently either the pressure in the system or the quantity of water necessarily introduced via conduit 21, or both, must increase markedly since the quantity of such non-condensable gases as carbon dioxide increases radically. The detrimental effect of this on the stripper-reabsorber system performance thus become manifest.

An illustration of this is provided by a consideration of a facility operating in accordance with the teachings of the above-mentioned Belgian patent in contrast to operation of the same facility in handling a less $CO_2$-rich reaction effluent such as that obtained by operation in accordance with French patent No. 1,555,797 or U.S. Pat. No. 3,083,213. To obtain a reabsorbate solution having a comparable ethylene oxide content from the $CO_2$-rich gaseous reaction effluent requires a 5% increase in the quantity of water fed to the reabsorber as well as a 23% increase in reabsorber overhead pressure; in consequence, glycol make (representing a yield loss) increases by about 8–10%. Stripper steam consumption would also increase.

Figure 2:
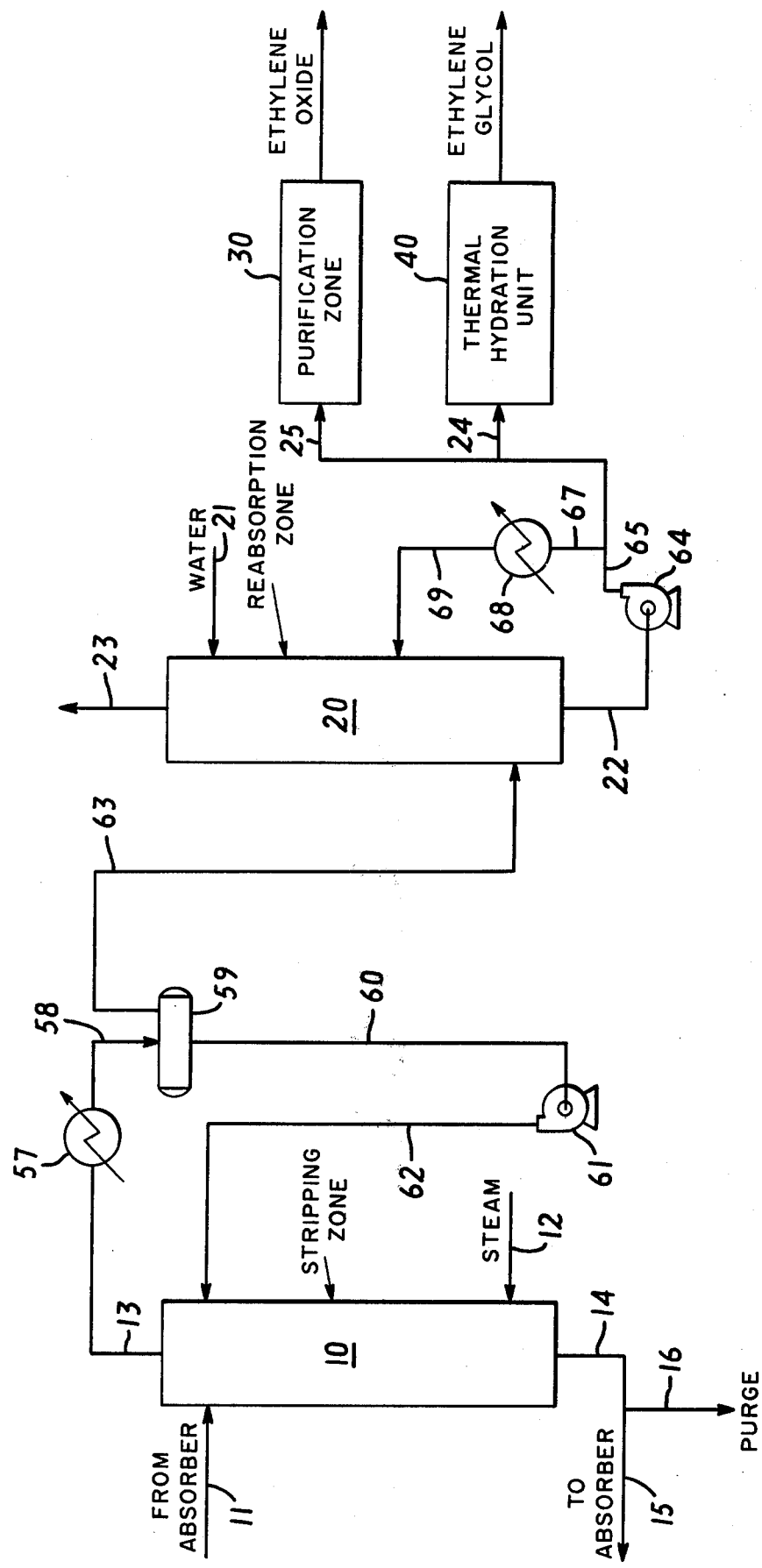
FIG. 2 is a schematic representation of a stripper-reabsorber system modified as provided by this invention; and, FIG. 3 is a schematic representation of a particularly preferred version of the embodiment set forth schematically in FIG. 2.

The process in accordance with this invention overcomes the disadvantages referred to above and is schematically depicted in FIG. 2. For ease of reference, processing equipment and conduits which are common both to the prior art (FIG. 1) and to this invention bear like reference numerals in both figures and will not herein be discussed in detail except where differences exist.

The configuration and operating characteristics for the stripper of the FIG. 2 embodiment are conventional and are as described in connection with FIG. 1. However, the stripper overhead vapor withdrawn from conduit 13 is treated differently. This overhead vapor is partially condensed in heat exchanger 57, and the vapor-liquid effluent from heat exchanger 57 is conducted via conduit 58 to vessel 59. Within vessel 59, the vapor and liquid phase are separated from each other. The liquid phase is withdrawn from vessel 59 via conduit 60 and is then returned by pump 61 via conduit 62 as reflux to an upper portion of stripper 10, preferably to the portion of stripper 10 where the absorbate is introduced.

In FIG. 2 embodiment, however, the absolute amount of steam supplied to the stripping zone via conduit 12 (or generated in situ) would be slightly higher than in the FIG. 1 embodiment. While the ratios of moles of steam supplied to the stripping zone per mole of entering absorbate remain unchanged, in the FIG. 2 embodiment these ratios are applied to the sum of moles of entering absorbate plus the moles of reflux returned via conduit 62 to the stripping zone. Since the amount of reflux is, on a molar basis, small in relation to the amount of absorbate, this increase in steam consumption is essentially negligible from an economic viewpoint.

Heat exchanger 17 of FIG. 1 and heat exchanger 57 of FIG. 2 are not exactly comparable in function. In the FIG. 1 embodiment, the extent to which the condensation is carried out is not of major importance; the lower the exit temperature from heat exchanger 17, the less will be load placed upon reabsorber 20, but stripper operation will be unaffected. Thus, the temperature of the material flowing through conduit 18 (the temperature to which the stripper overhead vapors are cooled in heat exchanger 17), can simply be set at the lowest level economically obtainable without the use of refrigeration, though refrigeration, either of the total coolant used in heat exchanger 17 or by use of a refrigerated after-cooler (not shown), can be used if desired. In this prior art embodiment cooling to a temperature less than that nominally desired does not harm and acts to further reduce the vapor load on reabsorber 20. In the FIG. 2 embodiment, however, the temperature of the material flowing through conduit 58 is usually at a temperature higher than that of the material flowing through conduit 18 of FIG. 1. That is, the extent of condensation within heat exchanger 57 is of major importance since if too little is carried out, the vapor feed to the reabsorber becomes excessive in quantity and too dilute in ethylene oxide, while if too much is carried out, the quantity of ethylene oxide condensed and recycled to the stripper becomes excessive and so, correspondingly, does the amount of glycol formed in the stripper.

While the drawbacks of excessive recycle of ethylene oxide to the stripper can be overcome to a large extent without increasing utilities requirements by incorporating additional vapor-liquid contacting stages within the stripper above the point at which the absorbate is introduced via conduit 11 to stripper 10 (these additional stages thus constituting a rectifying zone), the additional stages do increase capital cost and do not entirely prevent some incremental loss of yield because of increased pressure (and consequent higher temperature) in the lower portion of the stripper. In accordance with this invention, therefore, essentially at least about 50% of the water flowing through conduit 13 but not over about 20% of the ethylene oxide flowing through conduit 13 is condensed in heat exchanger 57. Desirably at least about 60% of the water but not over about 10% of the ethylene oxide and preferably at least about 80% of the water but not over about 7% of the ethylene oxide flowing through conduit 13 is condensed within heat exchanger 57. Control of the extent of condensation within heat exchanger 57 is, of course, readily accomplished, for example, by regulation of the coolant flow to heat exchanger 57. Assuming stripper operation at pressures within the normal range, from about 1.04 kg/cm$^2$ abs. to about 3.8 kg/cm$^2$ abs., the desired condensation is attained by cooling the stripper overhead vapor to a temperature from about 30° C. to about 80° C., desirably from about 35° C. to about 70° C. and preferably from about 40° C. to about 65° C., this of course being the temperature of the mixture of liquid and vapor flowing through conduit 58.

The uncondensed vapor, referred to in the balance of this specification and in the claims as the "partially condensed stripper overhead vapor," is withdrawn from vessel 59 via conduit 63 and is introduced to a lower portion of the reabsorber. Reabsorber 20 of FIG. 2 is entirely analogous to the correspondingly numbered reabsorber of FIG. 1, i.e., water is introduced to an upper portion of the reabsorber via conduit 21, non-condensed gases are vented from the top of the reabsorber via conduit 23 ad the reabsorbate is withdrawn from the bottom of the reabsorber via conduit 22. In FIG. 2, the reabsorbate flowing through conduit 22 has its pressure increased by pump 64 (the corresponding pump in FIG. 1 is not depicted) and thence flows through conduit 65 and is divided into two portions. That portion flowing through conduit 66 corresponds to the reabsorbate produced in the prior art, i.e., it is fed forward via conduit 25 to a purification step and/or it is fed forward tp a thermal hydration step via conduit 24. That portion of the reabsorbate flowing through conduit 67 is cooled in heat exchanger 68 and reintroduced, still as a liquid, to reabsorber 20 via conduit 69.

As hereinabove indicated, the quantity of reabsorbate flowing through conduit 69 is related to the quantity of material flowing through conduit 66 and must be such that at least 0.2 part by weight of reabsorbate is recycled (via conduit 69) per part by weight of reabsorbate fed forward (via conduit 66). More advantageous results are obtained when the weight ratio of recycled reabsorbate to reabsorbate fed forward for further processing is greater than the 0.2:1 figure hereinabove set forth. Desirably this ratio should be at least 0.1:1 and preferably should be at least 0.5:1. No process-based upper limits on this ratio exist, ratios as high as 20:1 being operative, though, of course, there are economic factors which make the use of excessively high ratios undesirable. These economic factors generally inhibit use of ratios in excess of about 10:1, and more favorable economics are obtained with ratios less than 8:1 and preferably less than 6:1. Especially outstanding results, in terms of a balance of process and economic considerations, are obtained with ratios of recycled absorbate to absorbate fed forward for further processing of from about 0.5:1 to about 2.0:1.

The amount of heat removed in heat exchanger 68 is such as to maintain the reabsorber in heat balance for the pre-determined reabsorbate concentration desired and will depend upon the amount and temperature of the scrubbing water introduced via conduit 21 in relation to the amount and temperature of the partially condensed stripper overhead vapor flowing through conduit 63 as well as the proportion of the ethylene oxide contained in the partially condensed stripper overhead vapor which is to be recovered in the reabsorber (usually over 99 mole % of the ethylene oxide is to be so recovered). Thus, it is not practicable to specify for all conditions the temperature of the liquid recycled reabsorbate, i.e., the temperature of the material flowing through conduit 69. Normally, however, the temperature to which the recycled reabsorbate is cooled in heat exchanger 68 would be less than the temperature of the partially condensed stripper overhead vapor introduced to the reabsorber via conduit 63 which is, neglecting heat losses to the surroundings, the same as the temperature of the material flow through conduit 58. A sizable temperature differential between the two materials is not necessary. Generally an adequate temperature differential between the materials flowing through conduit 69 and conduit 63 of even 2° C. would be adequate. To facilitate process control, however, a somewhat greater temperature differential would normally be employed. Accordingly, a temperature differential of at least 5° C., desirably at least 10°C. and preferably at least 15° C. would therefore be used. Still greater temperature differentials can, of course, be employed, though it would seldom be desirable or economic to use temperature differentials in excess of about 50° C. and preferably not in excess of about 40° C. In all events, however, the cooled reabsorbate for reintroduction must still be liquid.

The temperature differentials referred to in the preceding paragraph presuppose, however, that the partially condensed stripper overhead vapor exiting heat exchanger 57 is essentially at the same temperature as the material introduced to reabsorber 20 via conduit 63. Although not normally economic, an additional heat exchanger (not shown) can be used to further cool the materials flowing through conduit 63 prior to their introduction to the reabsorber, in which case this presupposition would no longer be correct. In this case, the temperature differentials just referred to would no longer apply and the recycled reabsorbate could then be at the same or at an even higher temperature than that of the partially condensed stripper overhead vapor; the only governing criterion would be maintenance of heat balance as indicated in the opening sentence of the preceding paragraph.

The number of theoretical vapor-liquid contacting stages and the necessary L/V ratio of the reabsorbers of the prior art have been discussed above in conjunction with FIG. 1. The reabsorber of this invention is operative with the same number of theorectical vapor-liquid contacting stages and the same L/V ratios as the reabsorbers of the prior art. Hence, these criteria need not again be here discussed. However, it is noteworthy that the point at which the liquid recycled reabsorbate is introduced to the reabsorber must be above the point at which the partially condensed stripper overhead vapor is introduced to the reabsorber so that there is at least 1 and preferably at least 2 theoretical vapor-liquid contacting stages between the two points, i.e., the point at which the recycled reabsorbate is introduced to the reabsorber is at least 1 theorectical vapor-liquid contacting stage above the point at which the partially condensed stripper overhead is reintroduced to the reabsorber. The provision of these stages between the points at which the partially condensed stripper overhead vapor and the recycled reabsorbate permits operation of the reabsorber at lower pressure, reduces the ratio of recycled reabsorbate fed forward for further processing, or permits the obtaining of a reabsorbate containing a greater concentration of ethylene oxide or any combination of the foregoing. It is often advantageous therefore to employ more stages between these two points. For example, up to 20 such stages can be employed. Favored practice calls for the provision of from 2 to 10 theorectical vapor-liquid contacting stages, and preferably from 3 to 8 such stages between the points at which the partially condensed stripper overhead vapor and the recycled reabsorbate are introduced.

It is also necessary to note that the extent of condensation within heat exchanger 57 and the quantity of recycled reabsorbate are interrelated. Thus, the greater the extent of condensation carried out within heat exchanger 57, the less will be the amount of recycled absorbate required and vice versa.

Figure 3:
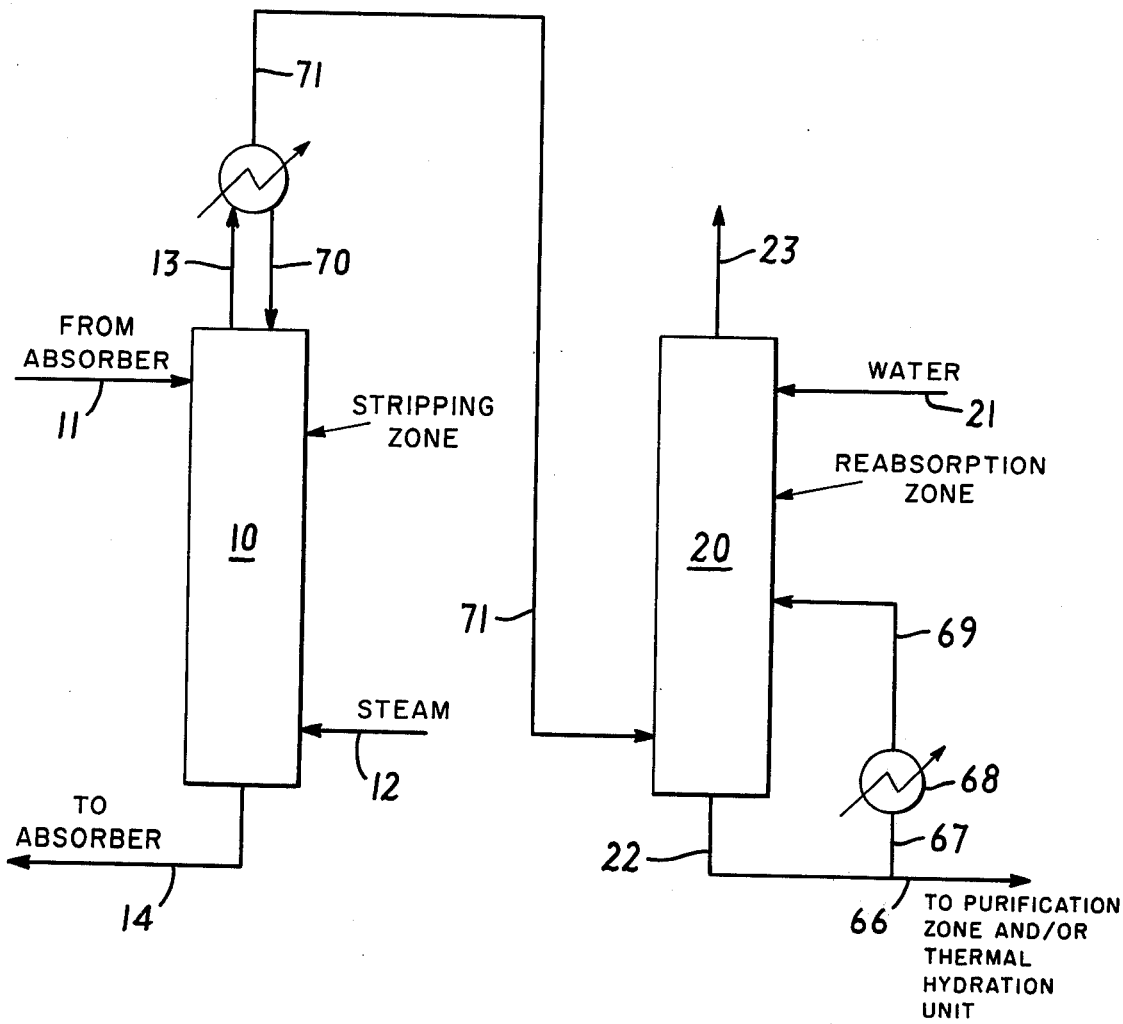

In FIG. 3 is shown a stripper reabsorber system identical in all respects to that of FIG. 2 but arranged so that vessel 59, pump 61 and conduit 62 are unnecessary. Elimination of these items of equipment is readily accomplished by physically locating heat exchanger 57 above stripper 10. Thus conduit 13 rises to heat exchanger 57 wherein the partial condensation occurs. The condensate drains under influence of gravity directly back to the top of stripper 10 via conduit 70. The uncondensed vapor is withdrawn from heat exchanger 57 via conduit 71 and is thence introduced to a lower portion of the reabsorber in a manner exactly comparable to the vapor flowing through conduit 63 of FIG. 2. It is also noteworthy that conduits 13 and 70 may themseleves be eliminated where heat exchanger 57 is physicaly connected to the part of stripper 10. This can be accomplished most readily by the insertion of cooling coils directly into an upper portion of stripper 10 at a point above which the absorbate is introduced via conduit 11 to the stripper.

As those skilled in the art will recognize, the annexed drawings are schematic in that fluid transfer devices, instrumentation, etc., are not generally therein depicted, since conventional. Further, as those skilled in the art will recognize, modifications to the systems depicted can readily be visualized. For example, the material flowing through conduit 63 of FIG. 2 or through conduit 71 of FIG. 3 can be further cooled in an additional (not illustrated) heat exchanger, thus reducing the amount of relcycled reabsorbate necessary and/or the amount of heat to be removed from the recycled reabsorbate in heat exchanger 68 as discussed above. This, though not normally economic, is feasible.

Throughout the foregoing description of the drawings, reference has often been made to the introduction of water to an upper portion of reabsorber 20. It should be noted that the water so introduced need not be pure since numerous water streams are available from various points in the process which can be used for this purpose. A typical suitable stream could contain substantial amounts of impurities, for example up to as much as 15-20 wt. % of ethylene glycol.

EXAMPLES

TABLE I

| Stream | Absorb. to Strip. (11) | Strip. Ov'h'd. Vapor (13) | Strip. Steam (12) | % wt. Strip. Bottoms (14) | Reflux to Strip. (70) | Partially Condensed Stripper Overhead Vapor (71) | Reabs. Bottoms (22) | Recyc. Reabsorbate (69) | Water Feed (21) | Vent Gas (23) | Net Reabs. Bottoms (66) |
|---|---|---|---|---|---|---|---|---|---|---|---|
| Temp., °C. | 97.4 | 99.6 | 119 | 114 | ~90 | 60 | 46.7 | 38 | 38 | 38 | 46.7 |
| Press., kg/cm² abs. | — | 1.51 | 2.03 | 1.69 | 1.51 | 1.51 | 1.41 | | 1.38 | 1.38 | |
| Flow, parts/hr. | 97.2 | 5.11 | 5.26 | 99.6 | 2.29 | 2.82 | 45.0 | 25.0 | 18.0 | 0.6 | 20.0 |
| Composition, % wt. | | | | | | | | | | | |
| Ethylene Oxide | 2.1 | 41.7 | — | — | 5.8 | 70.9 | 10.0 | 10.0 | — | nil | 10 |
| Carbon Dioxide | 0.6 | 11.4 | — | — | 0.1 | 20.6 | 200* | 200* | — | 91.9 | 200* |
| Water | 95.9 | 46.1 | 100.0 | 98.7 | 93.9 | 7.2 | 89.8 | 89.8 | 99.8 | 2.2 | 89.8 |
| Ethylene Glycol | 1.3 | 0.1 | — | 1.3 | 0.2 | — | 0.2 | 0.2 | 0.2 | — | 0.2 |
| Light Impurities & non-condensable gases | 0.1 | 0.7 | — | — | — | 1.3 | — | — | — | 5.9 | — |
| Heavy Impurities (as acetic acid) | 130* | 73* | — | 127* | 155* | 6.0* | 0.85* | 0.85* | — | — | 0.85* |

*Expressed in parts per million (ppm) by weight, not percent

The following examples are presented to further illustrate this invention but are not intended as limiting the scope thereof. Unless otherwise indicated, all flows are expressed on a weight basis. All liquid and vapor compositions, unless otherwise stated, are expressed on weight basis.

EXAMPLE I

Ethylene is continuously oxidized with molecular oxygen in the vapor phase in the presence of a silver catalyst in accordance with the teachings of Belgian patent No. 781,107 to generate a $CO_2$-rich gaseous reaction effluent containing over 40 mole % $CO_2$. This reaction effluent is cooled and scrubbed with water to generate an ethylene oxide-containing absorbate which also contains carbon dioxide, ethylene glycol (present by buildup of trace quantities formed during the absorption and subsequent stripping steps) and lesser amounts of dissolved non-condensable gases (ethylene, oxygen, nitrogen, argon, methane, ethane) as well as minor amounts of organic impurities (aldehydes and acids).

This absorbate is continuously processed in a stripper reabsorber system similar to that depicted in FIG. 3. The stripper employed contains 8 theoretical vapor-liquid contacting stages, while the reabsorber contains 15 theoretical vapor-liquid contacting stages. The recycled reabsorbate is introduced to the reabsorber at a point above that at which the partially condensed stripper overhead vapor is introduced, there being 5 theoretical vapor-liquid contacting stages between the two points. Temperatures, pressures, flow rates and stream compositions are given in the Table I which follows. The reference numerals appearing in parentheses below the stream identifications are those used in FIG. 3 and are provided to facilitate a cross-reference between this example and the drawing.

It should be noted that since the absorption is carried out at high pressure and the stripping at low pressure, a small portion of the absorbate vaporizes upon introduction to the stripper such that the actual absorbate fed to the stripper contains about 2 wt. % vapor. Examination of the foregoing data will indicate that over 98% of the ethylene oxide entering the system is recovered in the absorbate and less than 2% of the ethylene oxide is converted to ethylene glycol. The quantity of heavy impurities (aldehydes and acids) present in the reabsorbate is approximately one-twentieth of that present in the absorbate. Finally, the vent gas from the system is at a pressure sufficiently high to enable it to be vented or introduced, without compression facilities, into subsequent processing equipment.

EXAMPLE II

By way of comparison the following example, not illustrative of the invention, is presented. In this example the reactor effluent of Example I is treated to recover an absorbate of identical composition to that of Example I. This absorbate, however, is processed in a conventional prior art stripper reabsorber system like that depicted in FIG. 1. Process parameters for this comparative example are chosen to produce a reabsorbate of identical composition to that of Example I. In order to accomplish this, both stripper and reabsorber pressures are increased. In this instance, as in Example I, the stripping zone contains 8 theoretical vapor-liquid contacting stages while the reabsorber contains 15 such stages. Temperatures, pressures, flow rates, and stream compositions are given in Table II which follows. The reference numerals appearing in parenthesis below the stream identifications of Table II are those used in the description of FIG. 1 and are provided to facilitate a cross reference between this example and the drawing.

TABLE II

| Stream | Absorbate to Stripper (11) | Stripper Overhead Vapor (13) | Stripping Steam (12) | Stripper Bottoms (14) | Reabsorber Feed (18) | Reabsorber Bottoms (22) | Water Feed (21) | Vent Gas (23) |
|---|---|---|---|---|---|---|---|---|
| Temp., °C. | 103.4 | 106 | 126 | 120 | 38 | 50.7 | 38 | 38 |
| Press., kg/cm² abs. | — | 1.86 | 2.4 | 2.04 | 1.80 | 1.76 | 1.73 | 1.73 |
| Flow, parts/hr. | 97.2 | 4.84 | 5.0 | 97.3 | 4.84 | 20.0 | 15.8 | 0.6 |
| Composition, % wt. | | | | | | | | |
| Ethylene Oxide | 2.1 | 41.3 | — | — | 41.3 | 10 | — | — |
| Carbon Dioxide | 0.6 | 12.0 | — | — | 12.0 | 200* | — | 92.3 |
| Water | 95.9 | 45.9 | 100.0 | 98.7 | 45.9 | 89.8 | 99.8 | 1.8 |

TABLE II-continued

| Stream | Absorbate to Stripper (11) | Stripper Overhead Vapor (13) | Stripping Steam (12) | Stripper Bottoms (14) | Reabsorber Feed (18) | Reabsorber Bottoms (22) | Water Feed (21) | Vent Gas (23) |
| --- | --- | --- | --- | --- | --- | --- | --- | --- |
| Ethylene Glycol | 1.3 | — | — | 1.3 | — | 0.2 | — | — |
| Light Impurities & non-condensable gases | 0.1 | 0.8 | — | — | 0.8 | — | 0.2 | 5.9 |
| Heavy Impurities (as acetic acid) | 130* | 73* | — | 126* | 73* | 18* | — | — |

*Expressed in parts per million (ppm) by weight, not percent

Inspection of the data presented above in comparison to that presented in Example I (Table I) indicates that about 20 times more impurities pass from the stripper to the reabsorber and are reflected in a considerably higher impurities concentration in reabsorbate. Further, the higher pressure system required to obtain the same reabsorbate concentration of ethylene oxide mandates a somewhat higher loss of ethylene oxide by thermal hydrolysis to form ethylene glycols in the stripping system.

EXAMPLE III

A further comparison, not illustrative of the invention, is conducted to process the absorbate employed in Example I, again using a conventional stripper reabsorber system like that depicted in FIG. 1. As in the prior examples, a stripper having 8 theoretical vapor-liquid contact stages and a reabsorber having 15 theoretical vapor-liquid contacting stages are used. In this comparative example, however, stripper and reabsorber pressures are maintained at a level identical with that of Example I in order to minimize the amount of ethylene oxide hydrolysis which occurs. Table III, which follows, presents the temperatures, pressures, flow rates, and stream compositions encountered. Again, reference numerals, which appear in parenthesis below the stream identifications, are provided to facilitate a cross reference between this example and FIG. 1 of the drawing.

complex than would be the case in recovering ethylene oxide from the reabsorbate of either Example I or II.

EXAMPLE IV

This example is presented to further illustrate the invention and is not a comparative example. Ethylene is continuously oxidized with molecular oxygen in the vapor phase in the presence of a silver catalyst in accordance with the teachings of U.S. Pat. No. 3,083,213 to generate a reaction effluent containing only conventional quantities of $CO_2$ (less than 15 mole %). This reaction effluent is cooled and scrubbed with water to generate an ethylene oxide-containing absobate which also contains carbon dioxide (in lesser amounts than present in the absorbate used in Examples I–III, inclusive), ethylene glycols, and lesser amounts of dissolved non-condensable gases (ethylene, oxygen, nitrogen, argon, methane, ethane) as well as minor amounts of organic impurities (aldehydes and acids).

This absorbate is continuously processed in a stripper reabsorber system similar to that depicted in FIG. 3, with the stripper having 8 theoretical vapor-liquid contacting stages and the reabsorber having 15 theoretical vapor-liquid contacting stages. Again, the recycled reabsorbate is introduced to the reabsorber at a point above that at which the partially condensed stripper overhead vapor is introduced, there being 5 theoretical vapor-liquid contacting stages between the two points. Temperatures, pressures, flow rates, and stream com-

TABLE III

| Stream | Absorbate to Stripper (11) | Stripper Overhead Vapor (13) | Stripping Steam (12) | Stripper Bottoms (14) | Reabsorber Feed (18) | Reabsorber Bottoms (22) | Water Feed (21) | Vent Gas (23) |
| --- | --- | --- | --- | --- | --- | --- | --- | --- |
| Temp., °C. | 97.4 | 99.6 | 119 | 114 | 38 | 48.3 | 38 | 38 |
| Press., kg/cm² abs. | — | 1.51 | 2.03 | 1.69 | 1.45 | 1.41 | 1.38 | 1.38 |
| Flow, parts/hr. | 97.2 | 4.84 | 5.0 | 97.3 | 4.84 | 24.0 | 19.8 | 0.6 |
| Composition, % wt. | | | | | | | | |
| Ethylene Oxide | 2.1 | 41.3 | — | — | 41.3 | 8.34 | — | — |
| Carbon Dioxide | 0.6 | 12.0 | — | — | 12.0 | 200* | — | 91.9 |
| Water | 95.9 | 45.9 | 100.0 | 98.7 | 45.9 | 91.46 | 99.8 | 2.2 |
| Ethylene Glycol | 1.3 | — | — | 1.3 | — | 0.2 | 0.2 | — |
| Light Impurities & non-condensable gases | 0.1 | 0.8 | — | — | 0.8 | — | — | 5.9 |
| Heavy Impurities (as acetic acid) | 130* | 73* | — | 126* | 73* | 15* | — | — |

*Expressed in parts per million (ppm) by weight, not percent

The foregoing data clearly illustrate the advantages of this invention especially with respect to reabsorber bottoms concentration which, in this example, is substantially more dilute in ethylene oxide than that of either Example I or II. Recovery of ethylene oxide from such a reabsorbate is substantially more expensive and positions are given in Table IV which follows. The reference numerals provided below the stream identifications are those used in FIG. 3 and are provided to facilitate a cross reference between this example and the drawing.

TABLE IV

| Stream | Absorb. to Strip. (11) | Strip. Ov'h'd. Vapor (13) | Strip. Steam (12) | Strip. Bot-Toms (14) | Reflux to Strip. (70) | Partially Condensed Stripper Overhead Vapor (71) | Reabs. Bottoms (22) | Recyc. Reabsorbate (69) | Water Feed (21) | Vent Gas (23) | Net Reabs. Bottoms (66) |
|---|---|---|---|---|---|---|---|---|---|---|---|
| Temp., °C. | 97.4 | ~100 | 119 | 114 | ~90 | 60 | 46.7 | 38 | 38 | 38 | 46.7 |
| Press., kg/cm² abs. | — | 1.51 | 2.03 | 1.69 | 1.51 | 1.51 | 1.41 | — | 1.29 | 1.29 | |
| Flow, parts/hr. | 117.6 | 5.27 | 6.20 | 121.4 | 2.86 | 2.41 | 44.5 | 26.8 | 15.6 | 0.3 | 17.7 |
| Composition, % wt. | | | | | | | | | | | |
|   Ethylene Oxide | 1.7 | 42.3 | — | — | 8.1 | 83.0 | 11.3 | 11.3 | — | nil | 11.3 |
|   Carbon Dioxide | 0.2 | 4.6 | — | — | 0.1 | 10.0 | 100* | 100* | — | 84.3 | 100* |
|   Water | 96.2 | 52.2 | 100 | 98.7 | 91.6 | 5.4 | 88.5 | 88.5 | 99.8 | 1.7 | 88.5 |
|   Ethylene Glycol | 1.9 | 0.1 | — | 1.3 | 0.2 | — | 0.2 | 0.2 | 0.2 | — | 0.2 |
|   Light Impurities & non-condensable gases | <0.1 | 0.8 | — | — | — | 1.6 | — | — | — | 14.0 | — |
|   Heavy Impurities (as acetic acid) | 105* | 61* | — | 80* | | 4.6* | 0.63* | 0.63* | — | — | 0.63* |

*Expressed in parts per million (ppm) by weight, not percent

The foregoing data dramatically illustrate the advantages accruing to this invention in handling conventional reaction effluents of low $CO_2$ content as well as reaction effluents of high $CO_2$ content. Even though stripper and reabsorber pressures remain essentially the same, a reabsorber bottoms containing a higher concentration of ethylene oxide is obtained than is obtained in Example I, with obvious operating economies as a result. Further, reabsorber operation is clearly more effective.

The foregoing description illustrates the methods of this invention whereby the flexibility and advantages thereof are obtained. It will be understood that modifications and variations thereof may be effected by those skilled in the art without departing from the spirit of this invention. Accordingly, it is intended that all matter contained in the foregoing description shall be interpreted as illustrative and not in a limiting sense.

What is claimed is:

1. In the process for recovering ethylene oxide from the gaseous reaction effluent produced in the silver catalyzed, vapor-phase, partial oxidation of ethylene with molecular oxygen, the recovery process comprising the steps of: (a) countercurrently contacting the effluent with an aqueous scrubbing solution thereby producing an ethylene oxide-containing absorbate, (b) stream stripping said absorbate within a stripping zone containing a plurality of vaporliquid contacting stages to generate an ethylene-oxide containing stripper overhead vapor and (c) reabsorbing the ethylene oxide within a reabsorption zone containing a plurality of vapor-liquid contacting stages by countercurrent contact of the stripper overhead vapor with water to generate a reabsorbate suitable for further processing to recover ethylene therefrom and for thermal hydration of the ethylene oxide dissolved in said reabsorbate to form ethylene glycols, the improvement which comprises:

a. Subjecting the stripper overhead vapor to a partial condensation so that at least about 50% of the water contained therein is condensed while less than 20% of the ethylene oxide contained therein is condensed and returning the condensate from the partial condensation as reflux to an upper portion of the stripping zone;

b. Introducing the uncondensed portion of the stripper overhead vapor to the reabsorption zone;

c. Cooling a portion of the reabsorbate; and, d. Recycling said cooled reabsorbate and introducing it to a point within the reabsorber intermediate between the points at which the uncondensed portion of the stripper overhead vapor and the water are introduced to the reabsorption zone, the amount of said cooled reabsorbate being at least 0.2 part by weight per part by weight of reabsorbate not cooled.

2. A process in accordance with claim 1 wherein the uncondensed portion of the stripper overhead vapor is not further cooled after the partial condensation of step (a) and the introduction of said vapor to the reabsorption zone and wherein the temperature of the cooled reabsorbate is less than the temperature of the uncondensed portion of the stripper overhead vapor.

3. A process in accordance with claim 2 wherein the difference between the temperature of the introduced vapor and the temperature of the cooled reabsorbate is at least 2° C.

4. A process in accordance with claim 3 wherein the temperature difference is at least 5° C.

5. A process in accordance with claim 1 wherein there is at least one theoretical vapor-liquid contacting stage between the point at which the uncondensed portion of the stripper overhead vapor is introduced to the reabsorption zone and the point at which the cold reabsorbate is introduced to the stripping zone.

6. A process in accordance with claim 5 wherein the number of theoretical vapor-liquid contacting stages between the two points is from 2 to 10.

\* \* \* \* \*

UNITED STATES PATENT AND TRADEMARK OFFICE
CERTIFICATE OF CORRECTION

PATENT NO. : 3,964,980
DATED : June 22, 1976
INVENTOR(S) : Brian Ozero

It is certified that error appears in the above-identified patent and that said Letters Patent are hereby corrected as shown below:

| | |
|---|---|
| Abstract, last line: | "readsorption" should be -- reabsorption -- |
| Col. 1, line 58: | "over higher" should be -- ever higher -- |
| Col. 4, line 37: | "from" should be -- form -- |
| line 67: | "to" should be -- of -- |
| Col. 5, line 20: | delete "via conduit 40" |
| line 62: | "with small" should be -- with only small -- |
| Col. 7, line 18: | "In FIG. 2" should be -- In the FIG. 2 -- |
| line 36: | "be load" should be -- be the load -- |
| line 46: | "not harm" should be -- no harm -- |
| Col. 8, line 42: | "tp" should be -- to -- |
| Col. 9, line 21: | "flow" should be -- flowing -- |
| line 55: | "ratio of the" should be -- ratio for the -- |
| Col. 10, line 8: | "reabsorbate fed" should be -- reabsorbate to net reabsorbate fed -- |
| line 41: | "seleves" should be -- selves --; "physicaly" should be -- physically -- |
| line 42: | "the part" should be "and part" |
| Col. 11, Table I: | delete "% wt." from fifth heading |
| Col. 15, line 45: | "stream" should be -- steam -- |
| line 53: | "ethylene therefrom" should be -- ethylene oxide therefrom -- |

Signed and Sealed this

Fifth Day of April 1977

[SEAL]

Attest:

RUTH C. MASON
*Attesting Officer*

C. MARSHALL DANN
*Commissioner of Patents and Trademarks*